United States Patent
Krieg et al.

(10) Patent No.: US 7,008,389 B2
(45) Date of Patent: Mar. 7, 2006

(54) APPARATUS AND METHOD FOR STABILIZING PELVIC RING DISRUPTION

(75) Inventors: James C. Krieg, Portland, OR (US); William B. Long, Portland, OR (US); Steven M. Madey, Lake Oswego, OR (US); Michael Bottlang, Portland, OR (US)

(73) Assignee: Legacy Emanuel Hospital & Medical Health Center, Portland, OR (US)

( * ) Notice: Subject to any disclaimer, the term of this patent is extended or adjusted under 35 U.S.C. 154(b) by 362 days.

(21) Appl. No.: 10/383,217

(22) Filed: Mar. 5, 2003

(65) Prior Publication Data

US 2004/0039321 A1 Feb. 26, 2004

Related U.S. Application Data

(60) Provisional application No. 60/362,036, filed on Mar. 5, 2002.

(51) Int. Cl.
*A61F 5/00* (2006.01)

(52) U.S. Cl. .............. 602/19; 602/23; 602/36; 128/99.1

(58) Field of Classification Search ............ 602/5, 602/19, 23–24, 32, 36, 38–39, 60, 67–68; 128/96.1, 98.1, 99.1, 100.1, 101.1, 869, 876; 2/311–322; 24/68 R, 585, 31 R, 32, 33, 36, 24/578.15, 579.09; 601/71, 124
See application file for complete search history.

(56) References Cited

U.S. PATENT DOCUMENTS

| | | | |
|---|---|---|---|
| 35,038 A | 4/1862 | Pierce | |
| 2,552,475 A | 5/1951 | Austlid | |
| 4,179,755 A | * 12/1979 | Clark | 2/322 |
| 4,459,979 A | * 7/1984 | Lewis, Jr. | 602/19 |
| 4,715,364 A | * 12/1987 | Noguchi | 128/96.1 |
| 4,747,399 A | * 5/1988 | Glomstead | 602/36 |
| 4,912,813 A | 4/1990 | Muller et al. | |
| 5,226,874 A | 7/1993 | Heinz et al. | |
| 5,232,424 A | * 8/1993 | Pearson et al. | 482/106 |
| 5,346,461 A | 9/1994 | Heinz et al. | |
| 5,407,422 A | 4/1995 | Matthijs et al. | |
| 5,437,618 A | 8/1995 | Sikes | |
| 5,500,959 A | * 3/1996 | Yewer, Jr. | 602/19 |
| 5,551,085 A | * 9/1996 | Leighton | 2/44 |
| 5,572,747 A | * 11/1996 | Cheng | 2/322 |
| 5,588,186 A | 12/1996 | Ko | |
| 5,647,824 A | * 7/1997 | Levenson | 482/92 |
| 5,690,122 A | 11/1997 | Weber-Unger | |
| 5,728,056 A | * 3/1998 | Seriguchi et al. | 602/19 |
| 5,782,781 A | 7/1998 | Nagaoka | |
| 5,913,410 A | 6/1999 | Tsuchiya | |
| 5,970,526 A | 10/1999 | Weathers | |
| 6,066,109 A | 5/2000 | Buser et al. | |
| 6,099,490 A | * 8/2000 | Turtzo | 602/19 |
| 6,554,784 B1 | * 4/2003 | Krieg et al. | 602/23 |
| 2001/0053884 A1 | * 12/2001 | Krieg et al. | 602/19 |

FOREIGN PATENT DOCUMENTS

WO    WO 90/05502    * 5/1990

* cited by examiner

*Primary Examiner*—Amanda Flynn
(74) *Attorney, Agent, or Firm*—Kolisch Hartwell, P.C.

(57) ABSTRACT

Apparatus and methods for stabilizing a fractured pelvis in an emergency using a sling having a buckle designed to automatically lock the circumference of the sling at a tension level that has been predetermined to be effective for stabilizing a fractured pelvis without excessive or potentially damaging compression.

21 Claims, 11 Drawing Sheets

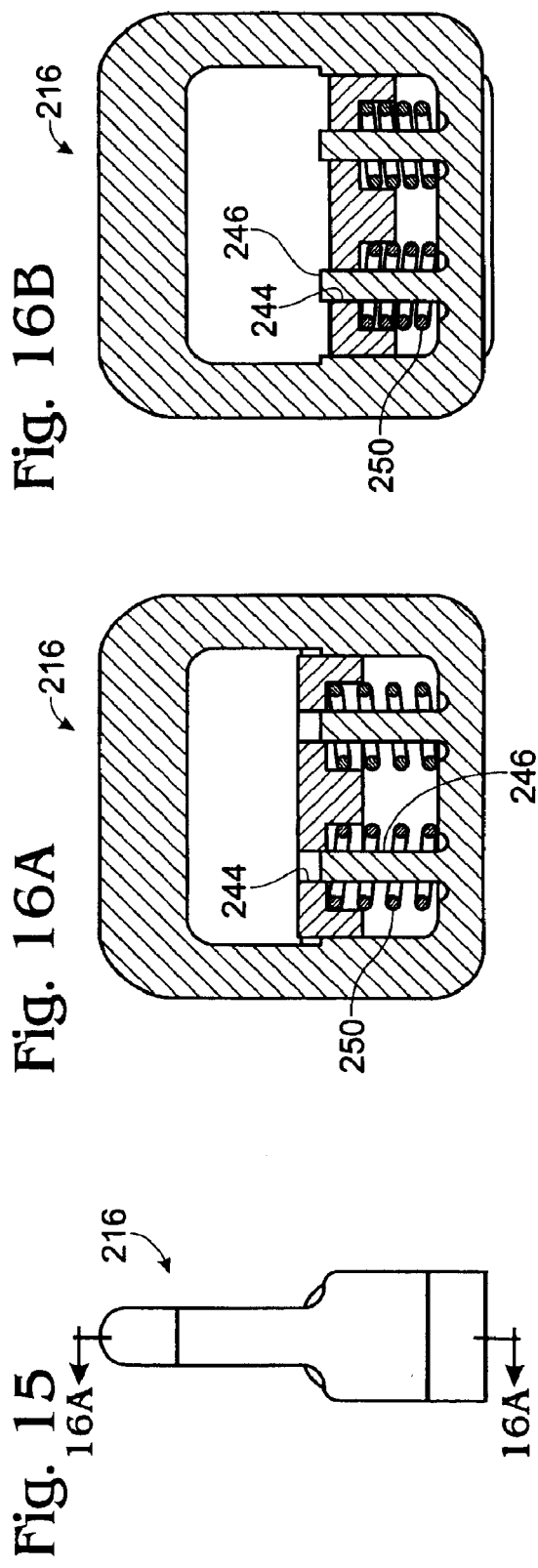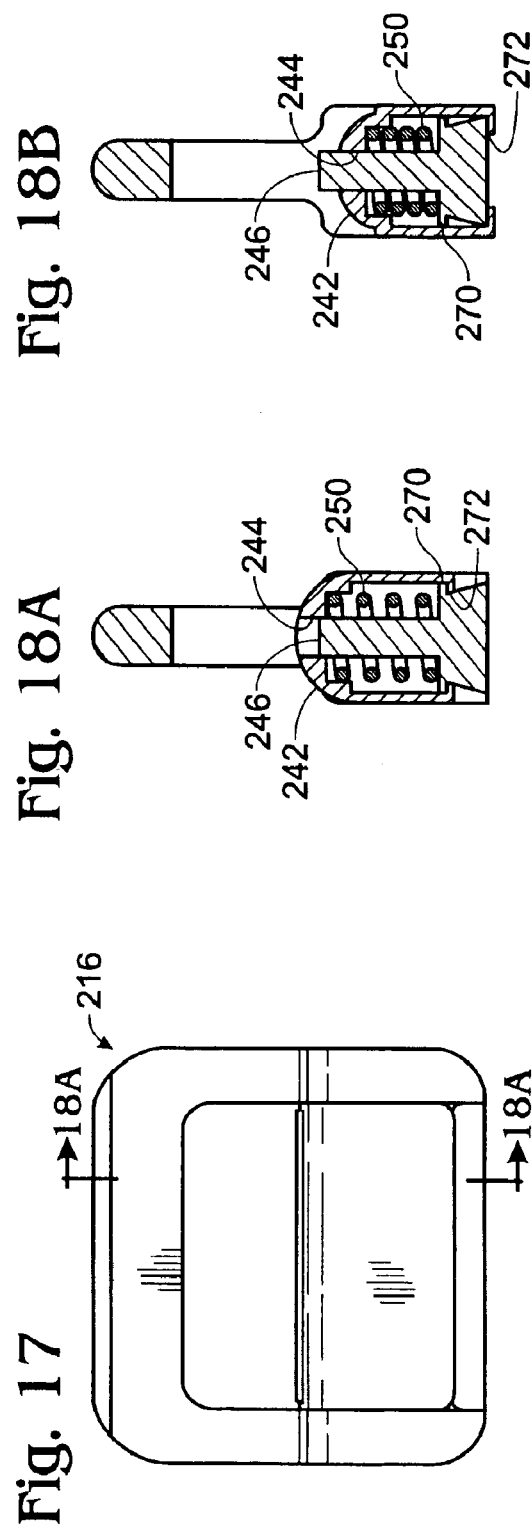

APPARATUS AND METHOD FOR STABILIZING PELVIC RING DISRUPTION

CROSS-REFERENCE TO RELATED APPLICATION

This application claims priority under 35 U.S.C. § 119 and applicable foreign and international law of the following U.S. provisional patent application which is hereby incorporated by reference in its entirety for all purposes: Ser. No. 60/362,036, filed Mar. 5, 2002. This application also incorporates by reference application Ser. No. 09/639,544, filed Aug. 16, 2000.

FIELD OF THE INVENTION

The invention relates to emergency treatment of a fractured pelvis. In particular, the invention provides a non-invasive sling device for reducing a fractured pelvis in a manner that minimizes internal bleeding.

BACKGROUND OF THE INVENTION

Many people die from internal bleeding due to a fractured pelvis. Achieving rapid hemodynamic stability in patients who have a fractured pelvis decreases the mortality rate substantially. Unfortunately, currently there is no satisfactory method or device for stabilizing a fractured pelvis in emergency situations outside a hospital. Pelvic stabilization at an emergency site within the first hour after the fracture occurs is critical and may often determine whether the patient lives or dies.

Stabilization of the pelvis is thought to be the most effective means to control bleeding for the following reasons. First, it decreases fracture fragment motion to prevent dislodgment of hemostatic clots and further tissue damage. Second, fracture reduction reopposes bleeding osseous surfaces, thus decreasing blood loss. Third, reduction decreases pelvic volume, thereby tamponading hemorrhage from the fracture and retroperitoneal tissue. Despite these widely recognized benefits, no adequate pelvic stabilization device for early management of pelvic fractures is currently available.

The current standard of care for treating pelvic trauma consists of fluid resuscitation, including appropriate use of blood products, angiography if necessary, and early invasive or non-invasive pelvic stabilization. Non-invasive pelvic stabilization techniques have been used. For example, a sheet may be wrapped around the pelvis and tied. Alternatively, a vacuum-type splinting device, or a pneumatic anti-shock garment may be used. These non-invasive techniques have a number of significant problems. One problem is that successful use and application of the device is quite dependent on the emergency caregiver. The person applying the device may not know how much compressive force to apply circumferentially around the pelvis. If too much force is applied, then the pelvis may be overly compressed causing significant complications. On the other hand, insufficient compressive force may leave the fractured pelvis unreduced, and therefore fail to adequately control internal bleeding. These problems are complicated by the fact that the emergency caregiver typically does not know what type of fracture has occurred. Different types of pelvic fractures may require different amounts of constructive tension to achieve optimal stabilization.

Another problem with some non-invasive pelvic stabilization devices is that they typically prohibit or restrict vital access to the abdomen, perineum, and lower extremity. Furthermore, prolonged application of devices such as the pneumatic anti-shock garment has been associated with significant complications, such as compartment syndrome of the lower limbs.

Invasive pelvic stabilization methods utilize external fixation, pelvic C-clamps, and open reduction and subsequent internal fixation. External fixation devices can effectively reduce and stabilize the pelvis and are relatively simple to apply.

Open reduction and internal fixation is the ultimate form of treatment for a fractured pelvis, and is considered the gold standard for accuracy of reduction, protection of neurovascular structures, and rigidity of fixation. However, its invasive nature makes it inappropriate for use in an emergency situation, such as the scene of a car accident, on the side of a mountain, or at a remote location of a traumatic fall where unstable pelvic ring disruptions require rapid pelvic reduction and temporary stabilization with limited information about the type or extent of internal injury. Therefore, invasive pelvic stabilization methods are used mainly in hospital operating rooms.

Accordingly, an object of the invention is to provide a method and apparatus for pelvic and stabilization that is non-invasive.

Another object is to provide a method and apparatus for pelvic stabilization that is capable of even and incremental application of hoop stress to both hemi-pelves while avoiding reactive forces that potentially can decrease the quality of reduction.

Another object of the invention is to provide a method and apparatus for pelvic reduction and stabilization that applies and maintains hoop stress around the pelvis at a preset and safe level, while avoiding the application of excessive hoop stress.

A further object of the invention is to provide a method and apparatus for stabilization of a fractured pelvis that can be applied in a rapid and simple manner by a single person without extensive training.

Still another object of the invention is to provide a method and apparatus for stabilizing a fractured pelvis that can be applied at an emergency site without the need for additional complex or heavy equipment.

Another object of the invention is to provide a method and apparatus for stabilizing a fractured pelvic in a nonintrusive manner, while allowing vital access to conduct other important emergency procedures on the patient.

Another object of the invention is to provide a method and apparatus that permits stable pelvic reduction prior to and during the application of a pelvic external fixator in the clinical setting.

SUMMARY OF THE INVENTION

The invention provides beneficial methods and apparatus for stabilizing a fractured pelvis in an emergency setting without requiring use of complex or invasive equipment. The invention may be used and carried out by a single person without extensive training or expertise.

The invention provides a sling device for stabilizing a fractured pelvis. A buckle is connected to a strap member to form a closed loop. The buckle has at least one automatic locking mechanism that allows the strap member to be tightened around a fractured pelvis until a predetermined threshold force is reached. The closed loop then maintains a substantially constant circumference until the strap member is released from the buckle.

The invention also provides a method of stabilizing a fractured pelvis. First, a belt is secured around a person's fractured pelvis. The tension of the belt is then automatically set at a level that has been predetermined to substantially reduce a fracture pelvis without excessive compression. In a preferred embodiment of the invention, the tension level of the belt is automatically set in the range of approximately 100 N to 180 N.

BRIEF DESCRIPTION OF THE FIGURES

FIG. 15 is a schematic side view of the buckle shown in FIG. 14.

FIGS. 16A and 16B are cross sectional views of the buckle shown in FIG. 15.

FIG. 17 is a front view of the buckle shown in FIG. 15.

FIGS. 18A and 18B are cross-sectional views of the buckle shown in FIG. 17, in the disengaged and engaged positions, respectively.

DESCRIPTION OF THE INVENTION

The invention includes many aspects that may be employed advantageously to stabilize a fractured pelvis in an emergency situation. Generally, the invention employs a compressive device that can be easily applied to a patient to provide an appropriate level of hoop stress so that the fractured pelvis is significantly reduced or at least stabilized but not overly compressed. Preferred examples and embodiments of the invention are described below with reference to the figures.

Figure 1:
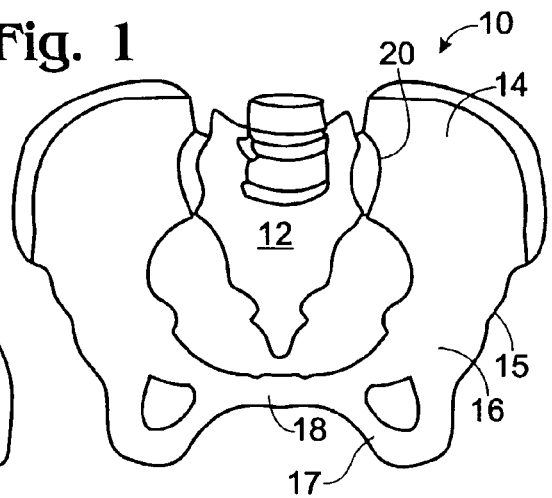
FIG. 1 is a front view of the pelvic ring.

FIG. 1 shows the bone structure that is referred to as the pelvic ring 10. The pelvic ring is formed by the sacrum 12, ilium 14, acetabulum 15, ischium 16, pubic rami 17, and symphysis pubis 18. Anteriorly, pelvic ring 10 contains a fibro cartilage joint. Posteriorly, the pelvic ring 10 contains the sacroiliac joints 20, which connect the sacrum 12 with the left and right ilium.

Figure 2A:
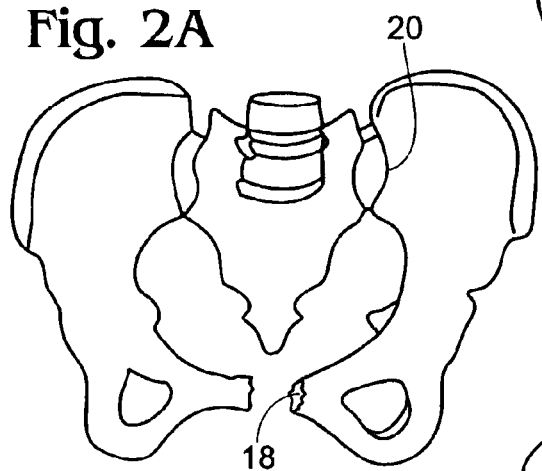
FIGS. 2A and 2B are front views of unstable pelvic ring disruptions.
Figure 2B:

Unstable pelvic ring disruptions are usually manifested by two or more fracture sites. In an "open-book" fracture, as shown in FIG. 2A, pelvic ring disruption is evident at symphysis pubis 18 and at one or both sacroiliac joints 20. FIG. 2B illustrates a lateral compression fracture in which pelvic ring disruption occurs at pubic rami 17 and at sacroiliac joint 20.

Figure 3:
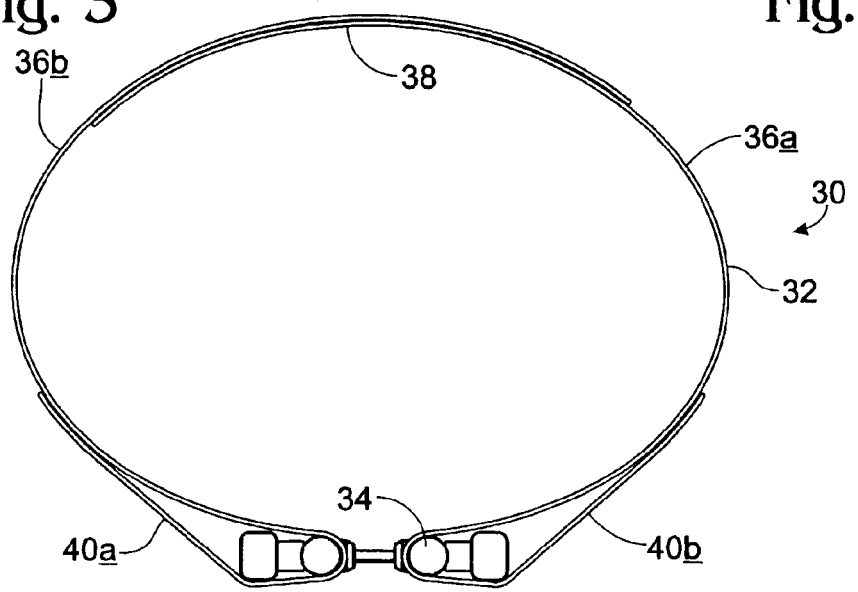
FIG. 3 is a top view of a pelvic sling.

FIG. 3 shows a top view of a sling 30 including a belt member 32 operatively combined with buckle device 34. Belt member 32 is comprised of two overlapping lateral portions 36a and 36b. Belt portions 36a and 36b have a variably overlapping region 38 for making gross adjustments to the circumference of the sling so that one sling device can be used on people of different sizes. Any appropriate mechanism may be used to provide variable overlap fixation of lateral belt portions 36a and 36b, for example, hook and loop type fasteners, for example, VELCRO™, may be utilized in overlapping region 38.

Figure 5:
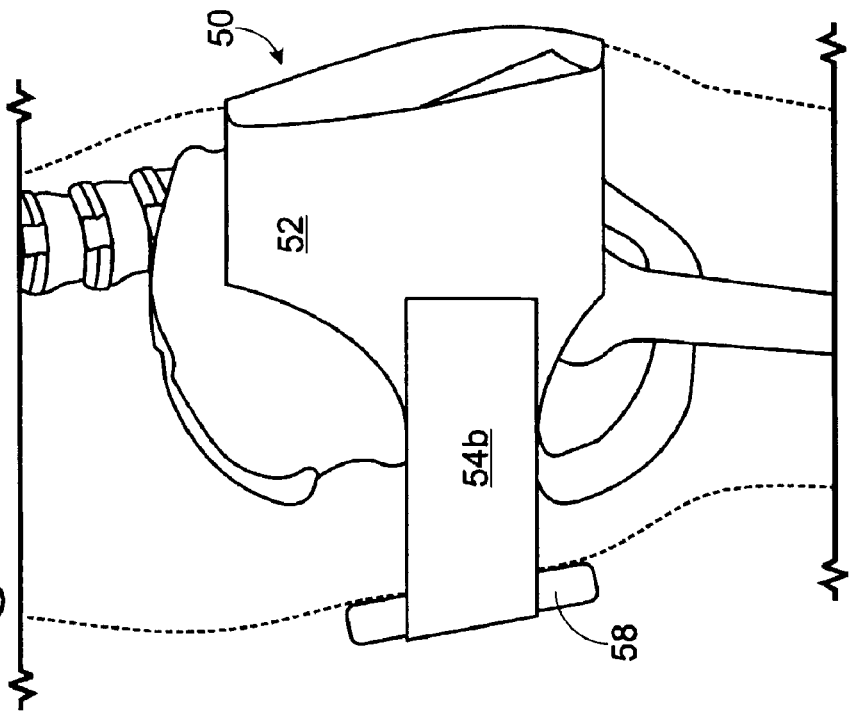
FIG. 5 is a side view of the sling and hipbone structure shown in FIG. 4.
Figure 4:
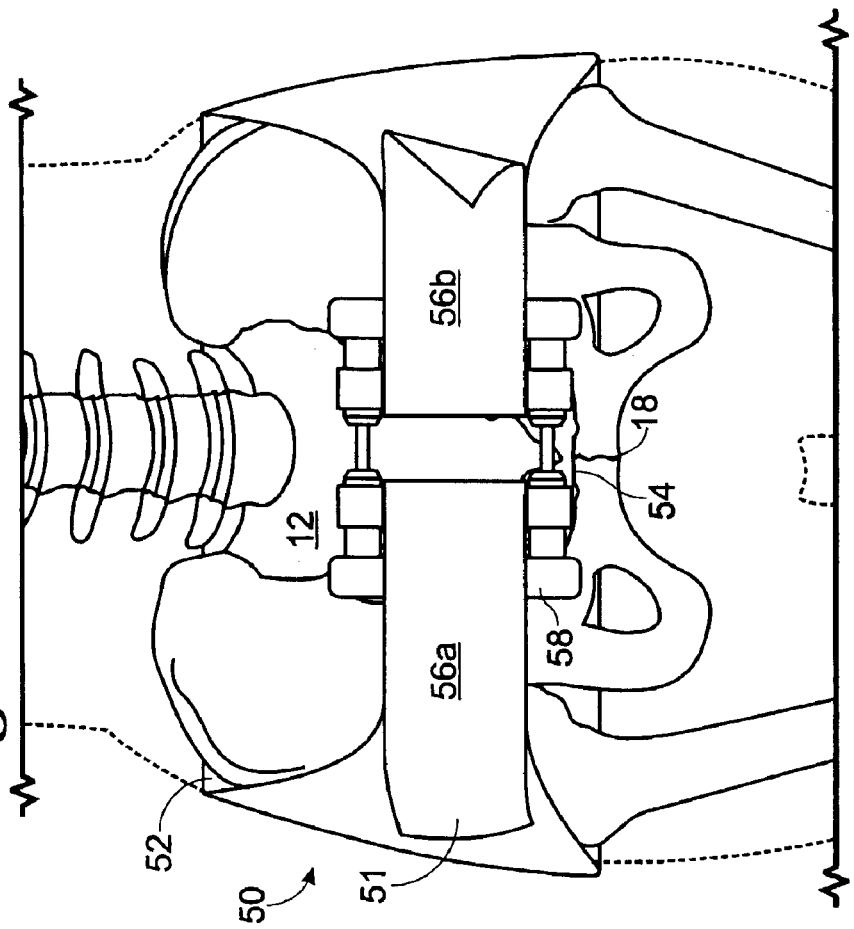
FIG. 4 is a front view of a pelvic sling applied to a fractured hip.

FIG. 4 is a front view of a pelvic sling shown in operative association with a human pelvis. FIG. 5 shows a side view of the same sling and pelvis of FIG. 4. Pelvic sling 50 has a belt portion 51 including an approximately 6-inch wide posterior sling component 52. Posterior sling component 52 is situated behind sacrum 12 with its lower edge located at the level of the superior rim 54 of symphysis pubis 18. Posterior sling component 52 is preferably made of a radiolucent material that is cushioned toward the skin interface to ensure a high degree of pressure distribution. The material is of sufficient stiffness to transmit tensile forces of at least 200 N without exhibiting strain larger than 10%. The material also has sufficient inherent elasticity to conform in part to body geometry. Posterior sling component 52 extends laterally toward the anterior portion of the abdomen. Symmetrical sling extensions 56a and 56b gradually decrease in width to approximately 2-inches as they circumvent the sides of the pelvis. The centerline of sling extensions 56a and 56b is approximately 2-inches above the lower edge of posterior sling component 52. Sling extensions 56a and 56b are directed through buckle 58 which is centered over the abdomen. Buckle 58 reverses the direction of both sling extensions 56a and 56b. Simultaneous application of sideward directed tensile force to each sling extension 56a and 56b yields in tensioning of the entire sling, which in turn induces even hoop stress around the pelvis. The hoop-stress subsequently reduces the geometric integrity of the disrupted pelvic ring and promotes stability of the fracture fragments. After application of sling tension at the appropriate level, the ends of sling extensions 56a and 56b are attached to lateral sling portions, for example, by hook and loop fasteners, to maintain sling tension.

Figure 6:
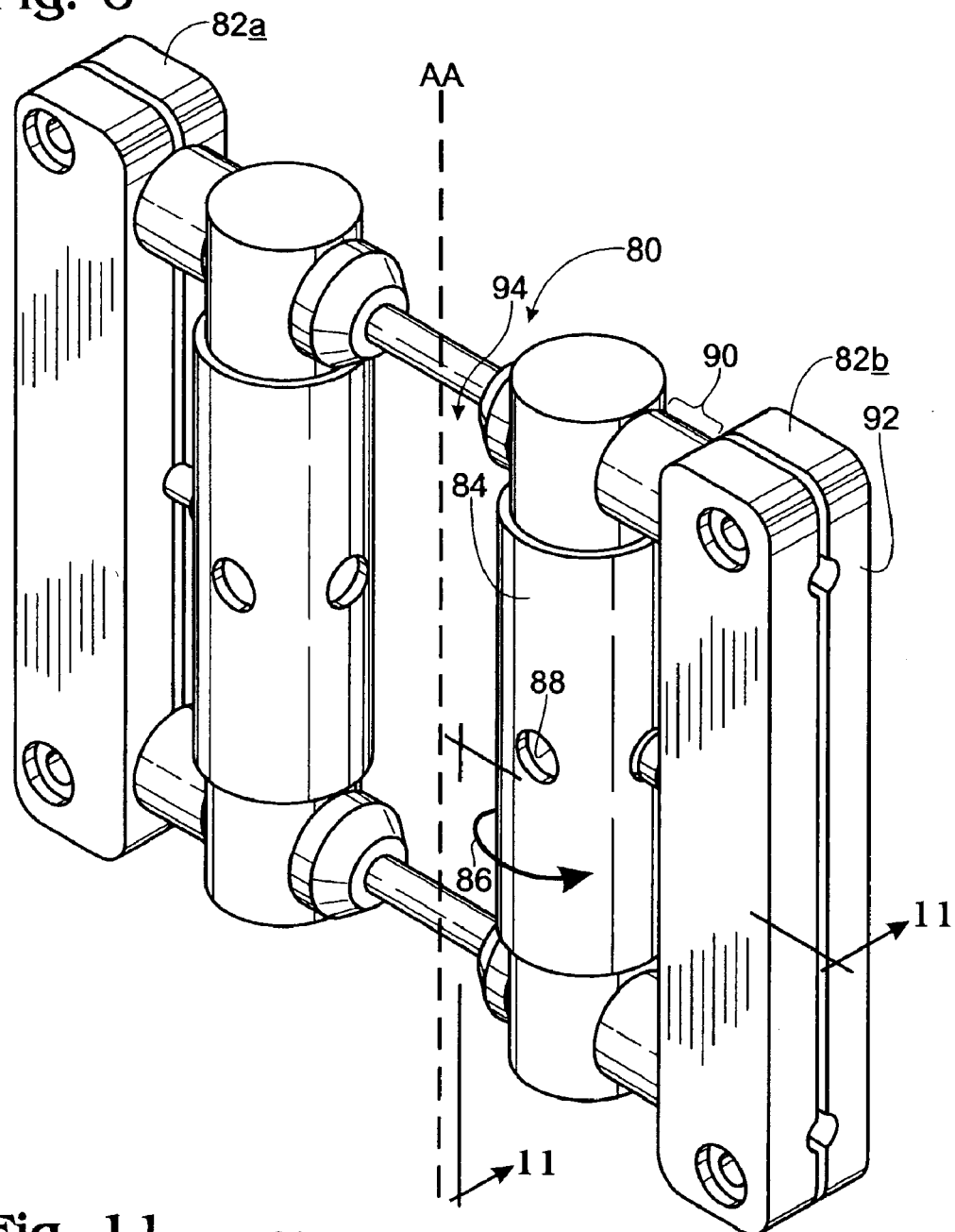
FIG. 6 is a perspective view of a buckle for use on a pelvic sling.

FIG. 6 shows a perspective view of a buckle design for use on a pelvic sling. Buckle 80 is characterized by sideto-side symmetry relative to axis AA. Each of lateral buckle portions 82a and 82b is designed to engage and secure an end of sling extensions 56a and 56b, respectively, at an appropriate tension level. The details described below in relation to lateral buckle portions 82b are the same for lateral buckle portion 82a, unless expressly distinguished.

Figure 7:
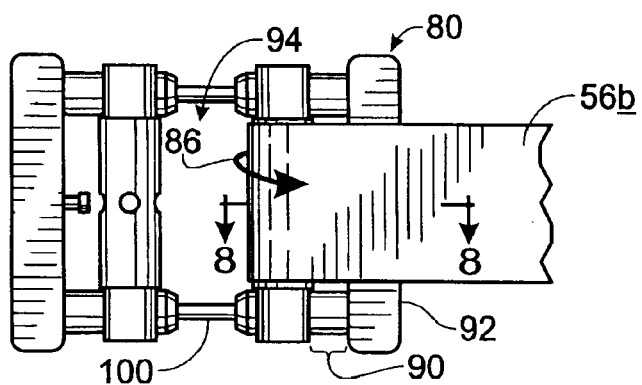
FIG. 7 is a partial front view of a sling showing one end portion of the sling engaging the buckle of FIG. 6.

Lateral buckle portion 82b includes rotating cylinder 84 that is free to rotate when buckle 80 is unlocked. As shown in FIG. 7, sling extension 56b wraps around cylinder 84. Cylinder 84 rotates in direction 86 when the sling is being tightened. Holes 88 are provided in cylinder 84, as shown in FIG. 6, for engaging a pin to lock rotation of cylinder 84 as described in more detail. Gap 90 is defined between cylinder 84 and side bar 92. Gap 90 is maintained by springs that are not shown in FIG. 11. As belt tension increases, cylinder 84 is pulled toward side bar 92, thereby decreasing gap 90. Eventually, a pin member extending from side bar 92 engages hole 88 in cylinder 84, causing rotation of cylinder 84 to lock. The surface of cylinder 84 is devised to frictionally hold and resist slipping of the belt material around cylinder 84 when rotation is locked.

Buckle 80 is preferably comprised of reliable and robust design components to enable reproducible sling application to a preset and safe tension level. Sling extensions 56a and 56b are inserted through center portion 94 of buckle 80 and reverted by means of cylinder 84. Cylinder 84 have a rough outer surface to provide a high friction interface for engaging sling extensions 56a and 56b. Cylinder 84 rotates with low friction on a polyethylene roller core (not shown). The roller cores can slide laterally on parallel guide rods 100.

Figure 8:
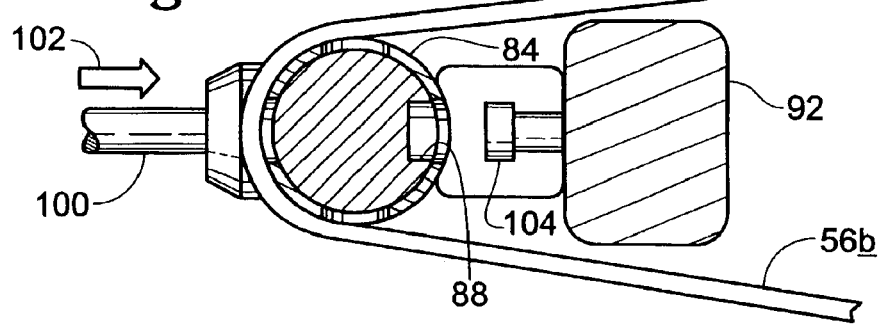
FIGS. 8–10 are cross-sectional views of the sling shown in FIG. 7, illustrating a mechanism for locking the tension of the belt.
Figure 9:
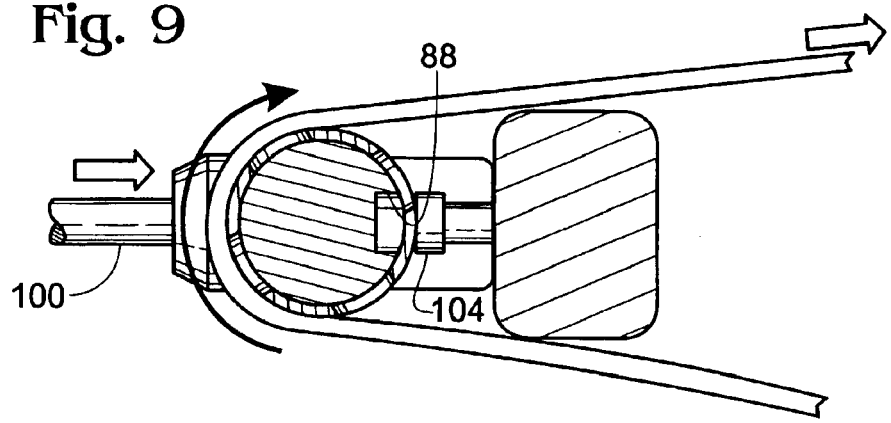
Figure 10:
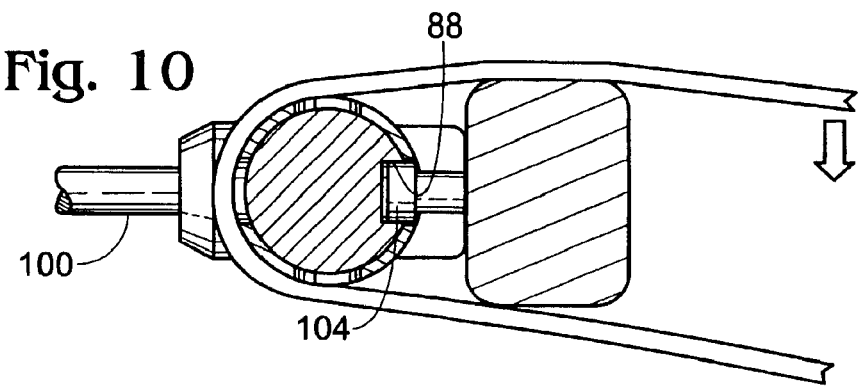

FIGS. 8–10 show cross-sectional views through the sling of FIG. 7, illustrating the mechanism for locking rotational movement of cylinder 84. Lateral translation of cylinder 84 on guide rod 100 in direction 102 causes lock pin 104 to engage holes 88 in cylinder 84, disabling further rotation of cylinder 84. This in turn disables further sling tensioning due to the high friction interface between sling extension 56b and the outer surface of cylinder 84. This feature of the sling device automatically and reproducibly sets the tension of the sling at a predetermined level. The preset tensioning level is in the range of 100 N to 180 N, preferably 140 N.

Once the sling tension level is reached, lock pin 104 engages hole 88 on cylinder 84 and enters a second hole of bigger diameter in cylinder 84. Lock pin 104 has a widened tip portion that engages the inner lumen of cylinder 84. Thus, even if the applied sling tensions decrease somewhat, cylinder 84 is not able to slide off lock pin 104, since cylinder 84 will impinge the widened tip portion of lock pin 104. Only if the applied sling tension decreases substantially will cylinder 84 be pushed off lock pin 104 by means of compression springs illustrated in FIG. 11. This design feature, referred to as "locking hysteresis," makes it possible to maintain the preset sling tension, even if the applied tension to the sling extensions decreases. An emergency technician can affix the ends of sling extensions 56a and 56b to the lateral sling portions without the need to maintain full sling tension for a prolonged amount of time, and without losing the preset sling tension.

Figure 11:
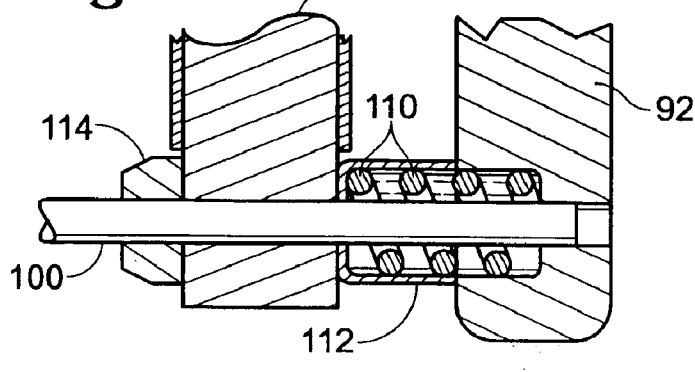
FIG. 11 is a partial cross-sectional view of the buckle shown in FIG. 6.

FIG. 11 shows another cross-section through buckle 80 of FIG. 7. Compression spring 110 counteracts lateral translation of cylinder 84 along guidepost 100. Compression spring 110 is mounted over guide rod 100, between side bar 92 and cylinder 84, and is covered by spring cage 112. This design component allows guided lateral translation of cylinder 84 against a pair of compression springs 110, only one of which is shown in FIG. 11. Collar 114 is located on the center region of guidepost 100. Collar 114 can plant rigidly to any site on guidepost 100 via screws. Collar 114 is used to hold each cylinder 84 in a laterally translated position, at which spring 110 is compressed to a preset value, for example 70N for each compression spring. Therefore, cylinder 84 will maintain its position during sling tensioning up to the preset force value, while sling extensions 56a and 56b are pulled over the respective rotating cylinders. Only if the sling tension exceeds the preset value, will lateral translation of cylinder 84 be induced.

The sling buckle components are preferably designed to be fabricated from non-metallic, radiolucent materials, excluding the cylinders, lock pins, and compression springs. This enables radiographic examination while maintaining pelvic reduction and stabilization.

The sling design constitutes two distinct components, the sling or belt and the sling buckle, which are combined in a functional unit with minimal effort. Different size-specific slings may be used with the same buckle. Furthermore, it may be desirable to provide a sling device in which the belt component is disposable and the buckle is reusable, or in which the entire sling including the buckle is disposable.

Figure 12:
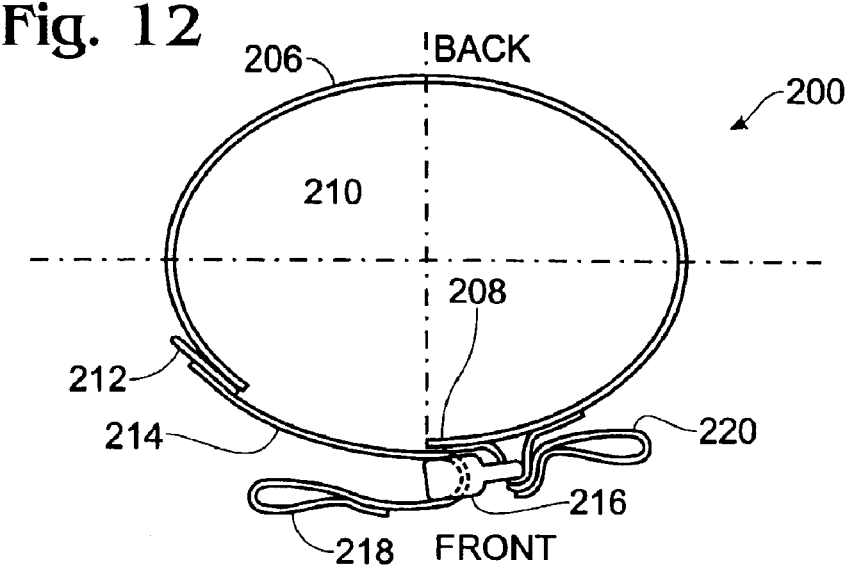
FIG. 12 is a top view of an alternative pelvic sling design according to the invention.

FIGS. 12–21 show an alternative embodiment of the invention. In FIG. 12 pelvic sling 200 includes main belt portion 206 for encircling at least about ¾ of a person's pelvis. Belt portion 206 has two ends 208 and 210. Mounting member 212 can be removably attached, for example, by VELCRO™, to different positions on belt portion 206. In FIG. 12 mounting member 212 is attached near end 210 of belt portion 206. Mounting member 212 is connected to strap member 214 which may be threaded through buckle 216. The end of strap member 214 has a loop or handle 218. Buckle 216 is mounted near end 208 of belt portion 206. A second handle 220 is connected to belt portion 206 near buckle 216 so that pelvic sling 200 may be tightened by pulling handles 218 and 220 in opposite directions.

Figure 13:
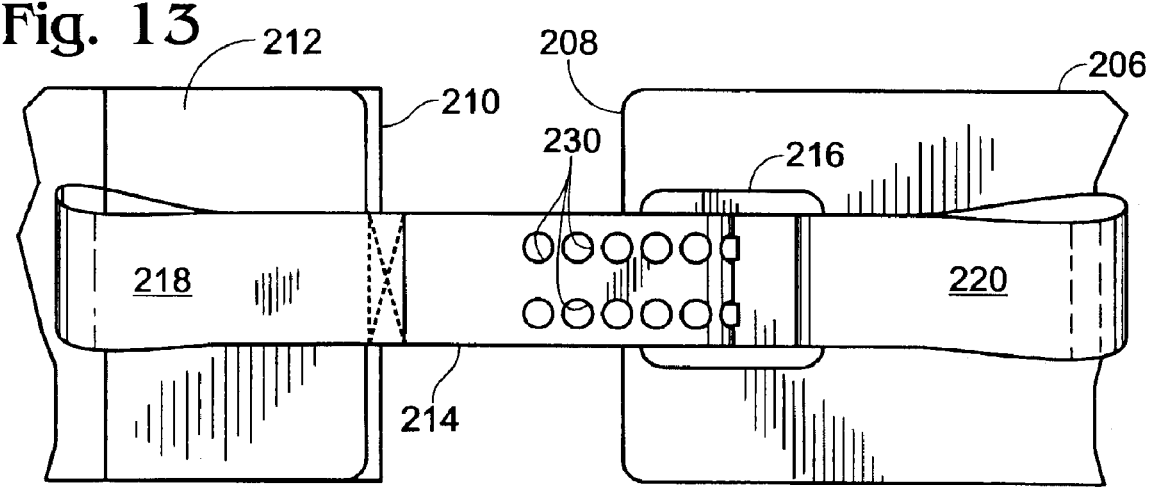
FIG. 13 is a partial front view of the pelvic sling shown in FIG. 12.

A partial front view of pelvic sling 200 is shown in FIG. 13. Strap member 214 has two rows of holes 230 for receiving spring biased pins in buckle 216.

Figure 14A:
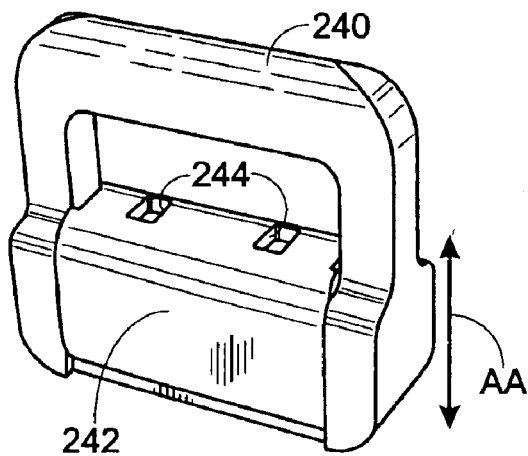
FIGS. 14A and 14B are perspective views of the buckle used in the pelvic sling shown in FIG. 12, in the disengaged and engaged positions, respectively.
Figure 14B:
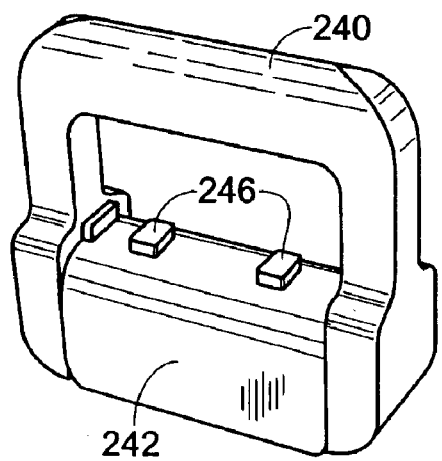
Figure 19:
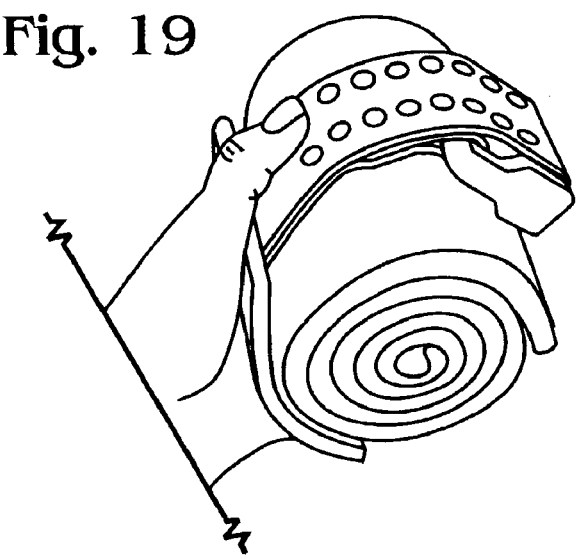
FIG. 19 is a perspective view of the pelvic sling as shown in FIG. 12, rolled up for storage.
Figure 20:
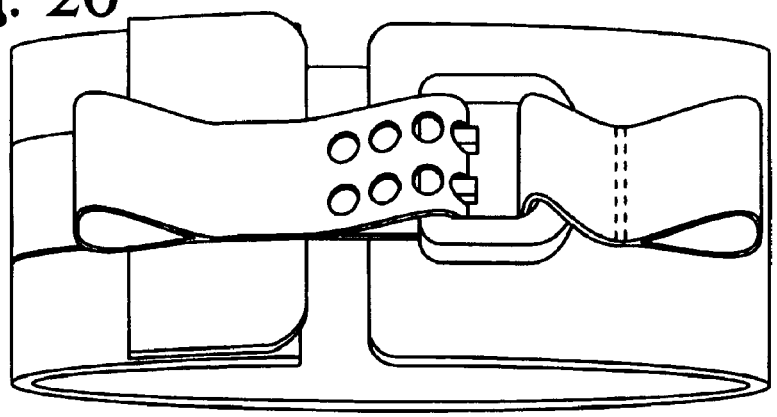
FIG. 20 is a front view of the pelvic sling shown in FIG. 12.
Figure 21:
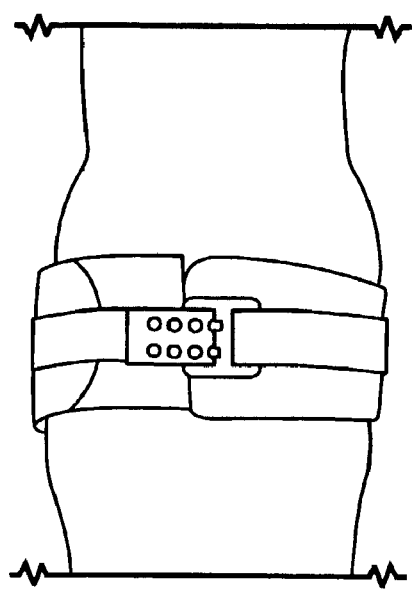
FIG. 21 is a front view of the pelvic sling shown in FIG. 12 strapped around a person's pelvis.

Perspective views of buckle 216 are shown in FIGS. 14A and 14B. Buckle 216 is made primarily from two parts, namely, rigid buckle frame 240 and sliding block 242. Sliding block 242 is movable in direction A—A relative to buckle frame 240. A pair of holes 244 are provided in sliding block 242. When strap member 214 is pulled against sliding block 242 internal springs are compressed, eventually resulting in extension of pins 246 through apertures 244, as shown in FIG. 14B. Pin structures 246 may then engage holes 230 in strap member 214.

FIGS. 18A and 18B show spring 250 positioned around one of pins 246. An identical spring 250 (not shown) is used on the other pin structure. FIGS. 18A and 18B show different sectional views of spring 250 in the disengaged and engaged positions, respectfully. Note that spring 250 in the disengaged position is already compressed significantly so that substantial force must be applied to sliding block 242 before it begins moving relative to buckle frame 240. Flange 270 on buckle frame 240 engages lip 272 of sliding block 242, thus retaining assembly of buckle frame 240 in sliding block 242 against the force of spring 250. When buckle 216 is engaged, as shown in FIG. 18B, lip 272 on sliding block 242 brackets bottom corners of buckle frame 240. This creates an audible "click" so that the user knows the buckle is engaged. Further, the flange bracketing creates a hysteresis affect which is explained in more detailed below.

In use, main belt portion 206 is placed around the back of a person's pelvis. Mounting member 212 is positioned at an appropriate location on the external side of belt portion 206, depending on the size of the patient. Strap member 214 is already pre-threaded through buckle 216. The caregiver then simply pulls handles 218 and 220 in opposite directions until the pins in buckle 216 emerge from holes 244 and engage holes 230 in strap member 214. Spring 250 is selected to have an appropriate spring constant, and length so that an optimal amount of force is required to engage buckle 216 with holes 230 in strap member 214. Studies have shown that the appropriate amount of tension is between 100 N to 180 N; or preferably between about 130 N to 150 N.

Pelvic sling 200 is made from a minimal number of components, and at minimal expense. The materials, except for the springs, are radiolucent. The sling design provides a completely assembled solution, ready for application.

Pelvic sling 200 uses a positive form-based locking design at a predetermined belt tension. The belt is guided over the semi-cylindrical surface of the sliding block. At a predetermined belt tension, the sliding block retracts so the two prongs advance through corresponding openings in the semi-cylindrical surface of the sliding block. The prongs engage equally-sized holes in a portion of the belt to prevent any further sliding of the belt over the sliding block. The holes in the belt have a slightly larger diameter than the prongs so that engagement occurs smoothly at the desired tension level.

Pelvic sling 200 requires a user to apply a predetermined sling tension of approximately 100 N to 180 N, at which point the prongs engage the perforated belt section. To facilitate definitive attachment of the belt end to the lateral belt portion by means of VELCRO™, the prongs stay engaged and hold the sling tension even if the user reduces the applied sling tension during the belt attachment procedure. Only if the sling tension is reduced by over about 50% will the prongs disengage which will yield an immediate release of pelvic circumferential compression. This hysteresis effect is achieved in part by friction between the engaged prongs and the belt and in part by a lip on the sliding block which partially engages rear corners of the buckle frame.

As soon as the predetermined belt tension is achieved, the lip of the sliding block will "snap" over edges of the buckle frame, which is accompanied by a clearly audible "click" sound. This sound intuitively provides the user with an audible feedback on the positive locking between the belt and the buckle, exactly at the time of the actual locking of the belt in the buckle.

Compressive springs are installed between the sliding block and the buckle frame to allow retraction of the sliding block and penetration of the prongs through the sliding block at a predetermined belt tension. The springs are installed with significant pre-tension. Therefore, even if the user applies a significant belt tension, the sliding block will not retract over the buckle frame. Only if the user applies a tension which approaches the desired locking tension, for example, approximately 140 N, will the sliding block retract. This pre-tension supports the user's intuitive feedback on positive locking, since only after a certain sling tension will the sliding block rapidly retract and prongs then quickly engage to stop the belt from further tensioning.

The belt buckle consists of one or more compression springs in two polyethylene parts (i.e., buckle frame and sliding block). The buckle is assembled by placing the springs on the buckle frame, and by snapping the sliding block over the springs on the buckle frame. Two lips on the sliding block engage edges on the buckle frame to provide permanent engagement. Disassembly can be achieved with a simple tool by prying the buckle frame and sliding block apart.

With exception of the compression springs, the belt buckle and the belt are radiolucent. The compression springs can be used as a radiographic index and documentation for the application and maintenance of sling tension. Alternatively, the compression springs might be replaced by a properly-dimensioned, oblique sliding surface on the buckle frame. This oblique surface will require the sliding block to expand upon retraction, where the amount of expansion can be dimensioned to yield the desired sling tension limit.

The assembled buckle constitutes a coherent, essentially rectangular unit with rounded edges and smooth surfaces. The design does not have exposed interfaces between moving parts, which could cause entrapment of fabric or pinching of skin during sling application. The buckle is permanently attached to one side of the belt. A tensioning handle on the opposite belt side is already engaged through the belt buckle. The tensioning handles are color coded in a bright fashion. Application of the sling requires three steps: (1) overlap and secure the belt end (mounting member 212) via VELCRO™; (2) pull the tensioning handles until the tensioning limit is reached; and (3) secure the tensioning handles via VELCRO™ to the medio-lateral belt portion. Pulling the buckle device in a second direction opposite from the first direction with approximately equivalent force minimizes significant shifting of the buckle device around the patient.

Figure 22:
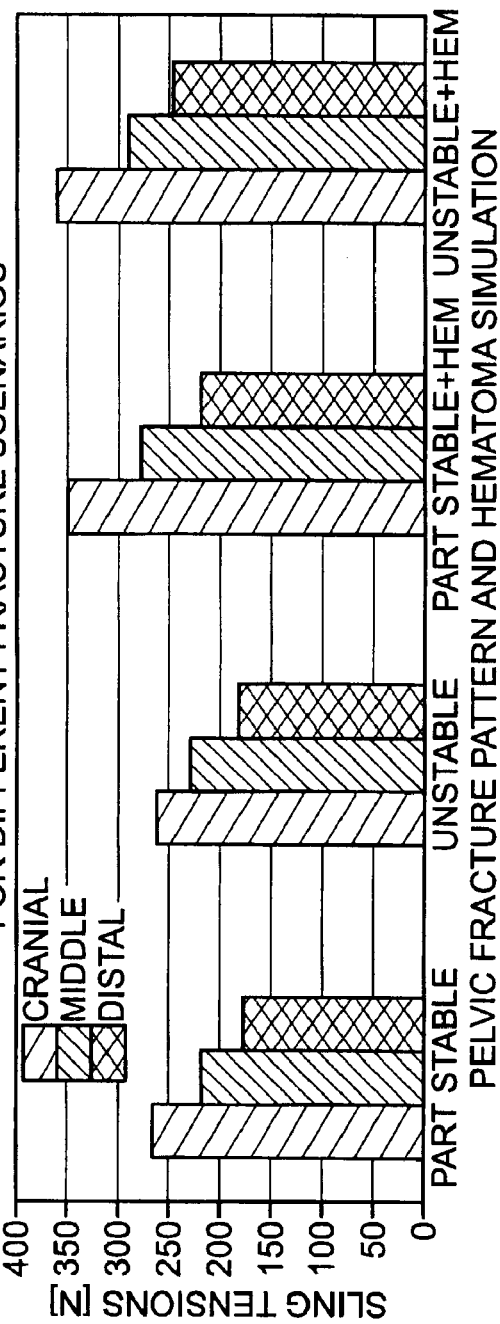
FIG. 22 is a graph illustrating the amount of tension required to reduce a fractured pelvis when the sling is applied at different locations.

An optimal sling location has been found to be within a transverse plane at the level of the greater trochanteric region, just proximal of the pubis symphysis. Application of a sling further distally is not feasible from a clinical perspective, disabling vital access to rectal and genital regions and the femoral artery. Application of a sling further proximally results in a significant decrease in the amount and quality of pelvic reduction corresponding to constant amounts of sling tension. FIG. 22 is a bar graph showing the results of an experiment to determine which sling location required the least sling tension to achieve pelvic reduction in different fracture scenarios. The graph shows that distal sling application, i.e., at the level of the acetabulum, required the least sling tension to achieve pelvic reduction in each of four different fracture scenarios: partially stable, unstable, partially stable and hemorrhaging, unstable and hemorrhaging.

Figure 23:
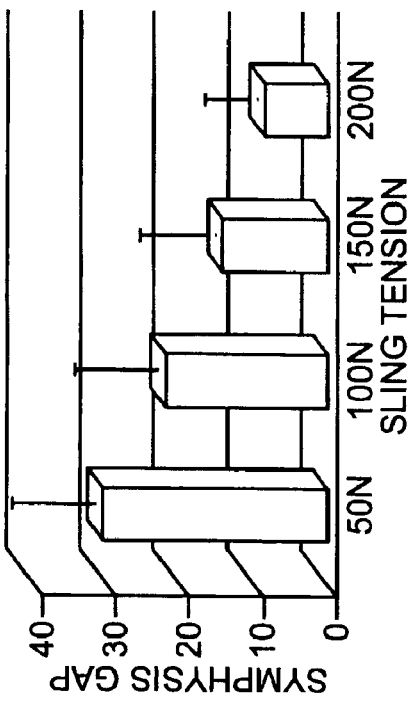
FIG. 23 is a bar graph illustrating the results of an experiment to determine the amount of sling tension required to adequately reduce the symphysis gap in an open-book pelvic fracture.
Figure 24A:
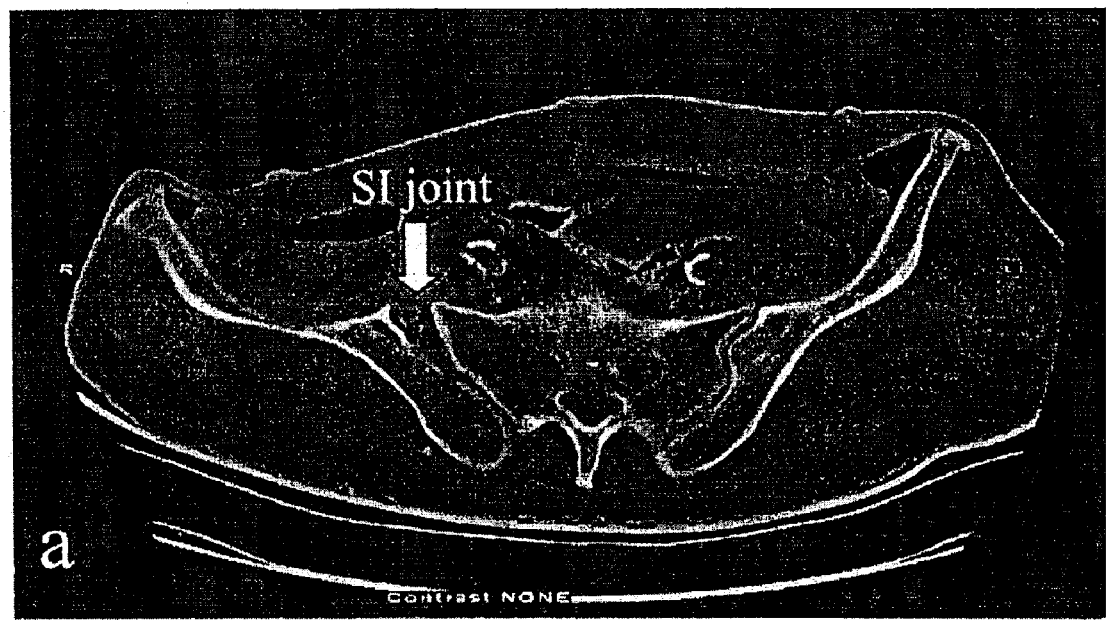
FIG. 24 is a set of four CT images showing a fractured pelvis before and after sling-induced reduction.
Figure 24B:
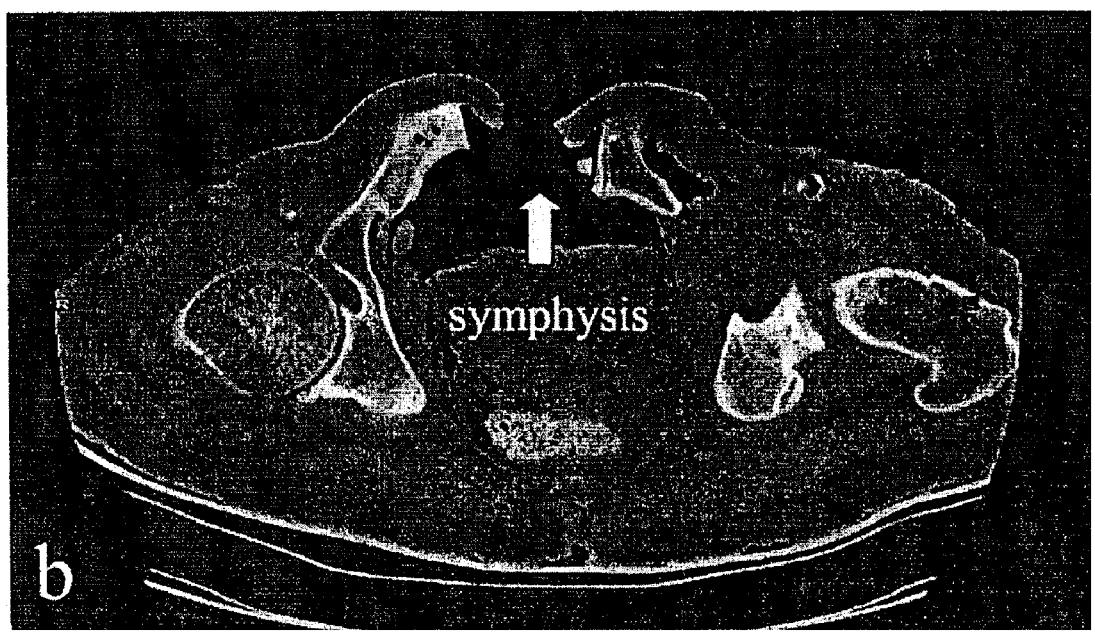
Figure 24C:
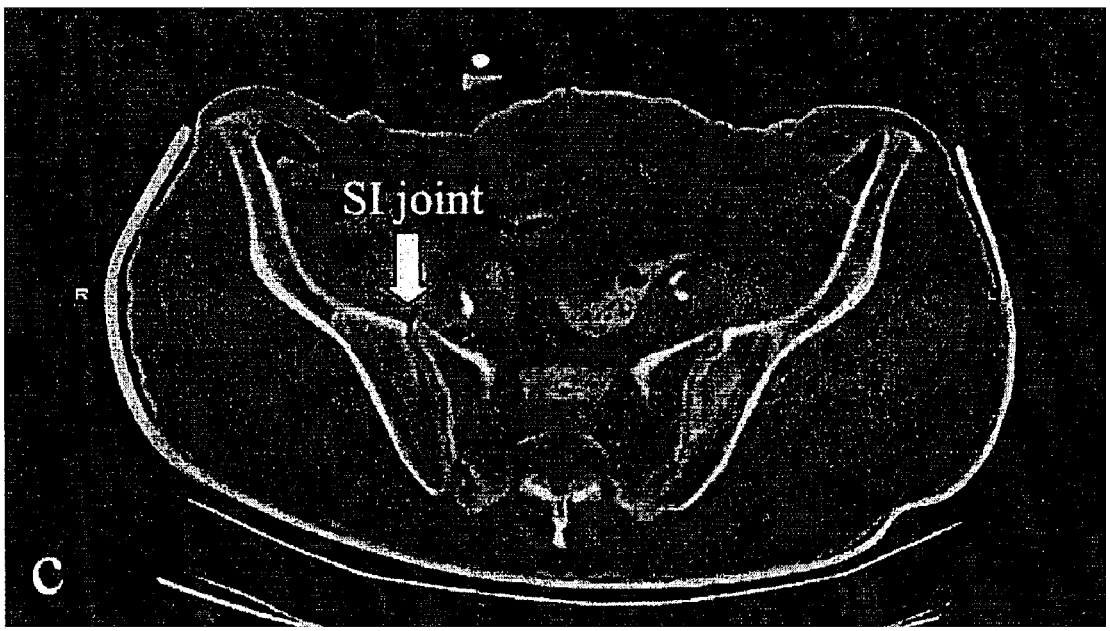
Figure 24D:
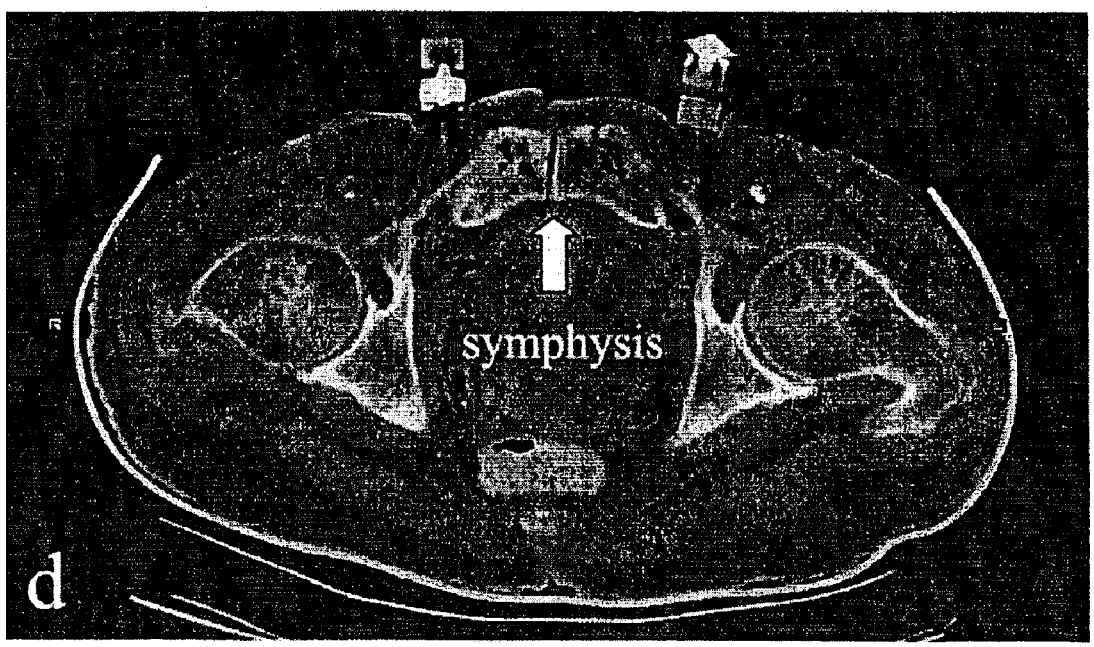

FIG. 23 shows a bar graph illustrating the results of an experiment to determine the relationship between sling tension and symphysis gap reduction for open-book fractures. A sling tension level of 200 N was required to reduce the symphysis gap to less than 10 mm.

FIG. 24 shows four CT images of a fractured pelvis. FIGS. A and B show the fractured pelvis prior to sling-induced reduction. The pelvic ring disruption is apparent by a widened SI joint in image (A) and a symphysis gap of 50 mm (B). As shown in images C and D, sling tension at the acetabular level at a tension of 200 N resulted in efficient translation of the applied sling tension into pelvic reduction.

Figure 25:
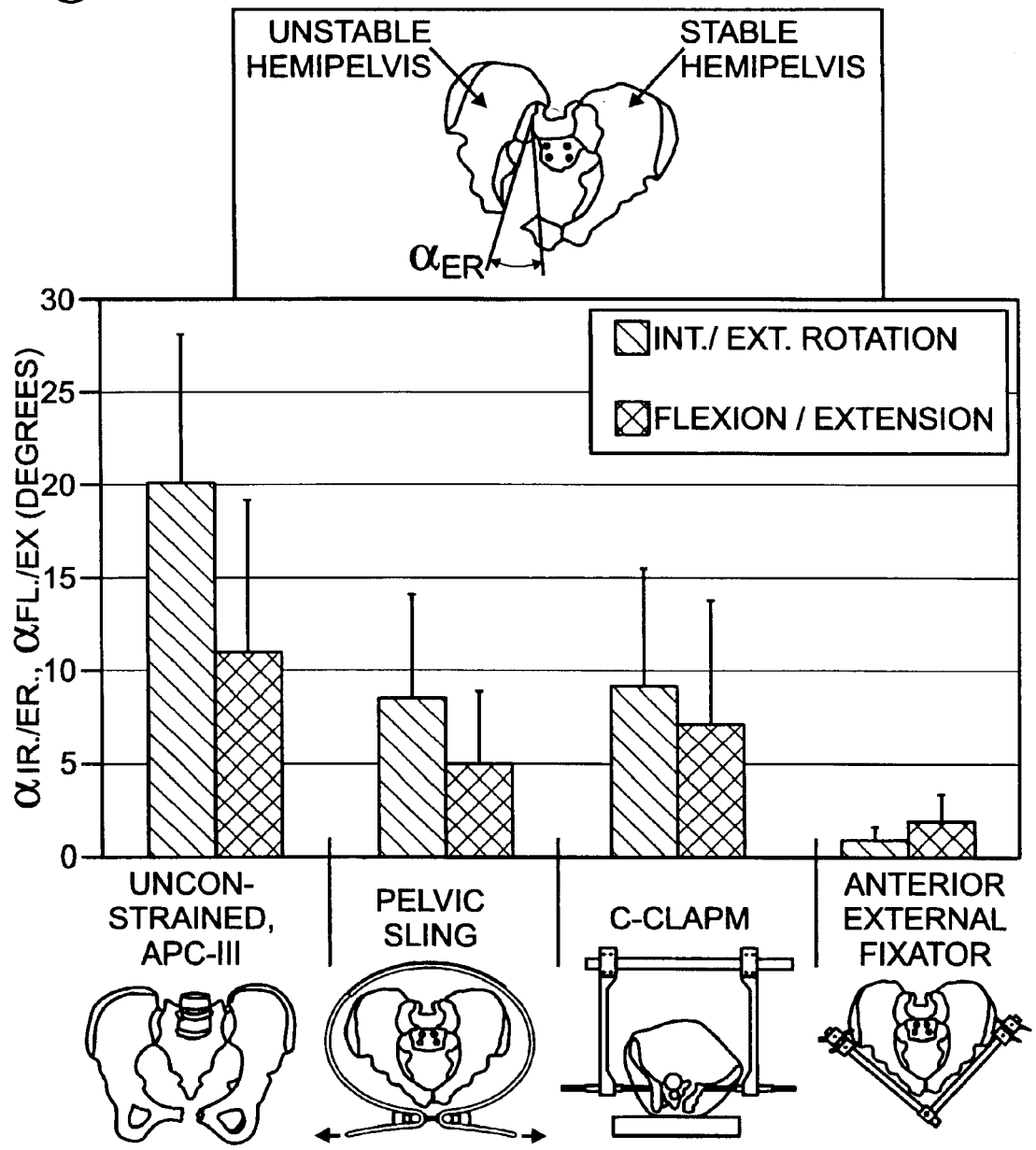
FIG. 25 is a bar graph showing the results of an experiment to compare the efficacy of various pelvic stabilizing techniques.

FIG. 25 shows the result of a biomechanical study to determine how much stabilization can be achieved with a non-invasive pelvic sling compared to invasive stabilization alternatives such as a C-clamp or an anterior external fixator. Unstable, unilateral open-book fractures (APC III, 100 mm symphysis diastasis) were created in eight non-embalmed human cadaveric specimens. Stabilization was provided first with the pelvic sling, applied around the greater trochanters, at a tension of 180 N. Subsequently, stabilization was provided with a posterior Pelvic C-clamp (Synthes, Monument, Colo.), and an anterior external fixator (Synthes, Paoli, Pa.). Stability was assessed in terms of the rotation of the unstable hemipelvis ($\alpha_{IR/ER}$, $\alpha_{FL/EX}$) in response to defined stress (9 Nm internal/external rotation or flexion/extension moments).

The bar graph in FIG. 25 shows that the pelvic sling significantly stabilized the open-book fractures and reduced fracture motion by up to 60%. The pelvic sling provided as much stabilization as the posterior Pelvic C-clamp. Compared to an external fixator, the pelvic sling provided ⅓ of the flexion-extension stability, but 10 times less internal/external rotation stability.

The experiments referred to in FIGS. 23 and 25 were conducted with cadavers with open-book pelvic fractures. Other types of pelvic fractures such as lateral compression fractures, as shown in FIG. 2B, are also common and may be treated with a pelvic sling in accordance with the invention. Fractures such as a lateral compression fracture should generally be treated with a lower tension level than may be used on an open-book fracture. For example, a 200 N tension may be used effectively on an open-book fracture, but could cause damaging overcompression on a lateral compression fracture. In an emergency situation, it is typically difficult if not impossible to diagnose the type of pelvic fracture. Therefore, it has been determined that the best strategy is to design the buckle to engage at a tension level that is slightly lower than may otherwise be optimally used on an open-book fracture. Accordingly, when treating a pelvic fracture in an emergency situation where it is unknown what type of fracture has occurred, the tension level should be between 100 N to 180 N, preferably 140 N. A 140 N tension level is sufficient to substantially stabilize a lateral compression fracture or an open-book fracture, without causing complications from excess compression, even though the symphysis gap may not be completely reduced.

Although the invention has been disclosed in its preferred forms, the specific embodiments thereof as disclosed and illustrated herein are not to be considered in a limiting sense, because numerous variations are possible. As used herein, singular terms do not preclude the use of more than one of the associated element, and embodiments using more than one of a particular element are within the spirit and scope of the invention. Applicants regard the subject matter of their invention to include all novel and nonobvious combinations and subcombinations of the various elements, features, functions, and/or properties disclosed herein. The following claims define certain combinations and subcombinations of features, functions, elements, and/or properties that are regarded as novel and nonobvious. Other combinations and subcombinations may be claimed through amendment of the present claims or presentation of new claims in this or a related application. Such claims, whether they are broader, narrower, equal, or different in scope to the original claims, also are regarded as included within the subject matter of applicants' invention.

We claim:

1. An apparatus for stabilizing a fractured pelvis comprising
    a belt including a strap and a buckle, the strap having a plurality of holes, the buckle including a base portion having one or more pins projecting from the base portion, the one or more pins being dimensioned to fit in the holes of the strap, a slide portion having a contact surface, the slide portion being mounted over the one or more pins and being moveable relative to the base portion, the slide portion being spring-biased toward a non-engaging position in which the one or more pins do not project beyond the contact surface of the slide portion allowing the strap to slide freely over the contact surface until sufficient force is applied to the slide portion so that it moves toward the base portion causing the one or more pins to project beyond the contact surface of the slide portion and engage one or more holes in the strap, thereby fixing the circumference of the belt at a preselected tension level.

2. The apparatus of claim 1, wherein the one or more pins emerge beyond the contact surface of the slide portion when a force between approximately 100 to 180 N is applied urging the slide portion toward the base portion.

3. The apparatus of claim 2, wherein the force required to cause the pins to project beyond the contact surface of the slide portion is approximately 140 N.

4. The apparatus of claim 1, wherein a spring mechanism urges the slide portion away from the base portion, the spring mechanism having a spring coefficient selected to supply an appropriate force to the slide portion so that the one or more pins engage the one or more holes of the strap when the belt is tensioned at a level that has been predetermined to be sufficient to stabilize a fractured pelvis without excessive compression.

5. The apparatus of claim 4, wherein the one or more pins engage the one or more holes of the strap when a force between approximately 100 to 180 N is applied urging the slide portion toward the base portion.

6. The apparatus of claim 1, wherein the base portion has two pins and the strap has two rows of holes for receiving the pins, the two pins being separated by the same distance as the two rows of holes.

7. The apparatus of claim 1 further comprising a pair of handles, one handle associated with the buckle and the other handle associated with the strap so that the belt can be tightened and secured by pulling the handles in opposite directions.

8. The apparatus of claim 1 further comprising
    a hook and loop fastening mechanism to secure an end of the strap when the one or more pins have engaged one or more of the holes of the strap.

9. The apparatus of claim 1, wherein the base portion and the slide portion form a compartment containing one or more springs that push the two portions apart, and a stop mechanism that prevents the two portions from completely disassociating.

10. The apparatus of claim 9, wherein the springs are partially compressed when no significant force is applied urging the slide portion toward the base portion.

11. The apparatus of claim 1, wherein the base portion has two pins, each pin having a coiled spring encircling the pin.

12. The apparatus of claim 1, wherein the strap has an enlarged width portion for contacting a person's back.

13. An apparatus for reducing a fractured pelvis comprising
    a buckle device,
    a first strap portion configured to encircle at least about ¾ of a person's pelvis, the first strap portion having a first end and a second end, the buckle device being attached to the first strap portion near the first end, and
    a second strap portion having a first end and a second end, the first end of the second strap portion being configured for adjustable overlapping hook and loop attachment to the second end of the first strap portion, the second end of the second strap portion having a first handle portion, wherein the buckle device has a second handle device, so that the apparatus can be approximately sized for a particular person by first adjusting the extent of overlap of the second end of the first strap portion with the first end of the second strap portion, followed by tightening the apparatus to a predetermined tension level by pulling the first and second handles in opposite directions.

14. The apparatus of claim 13, wherein at least one of the handles is formed by a strap loop.

15. The apparatus of claim 13, wherein the second strap portion has a plurality of holes, the buckle device including:

a base portion having one or more pins projecting from the base portion, the one or more pins being dimensioned to fit in the holes of the second strap portion, a slide portion having a contact surface, the slide portion being mounted over the one or more pins and being moveable relative to the base portion, the slide portion being spring-biased toward a non-engaging position in which the one or more pins do not project beyond the contact surface of the slide portion allowing the second strap portion to slide freely over the contact surface until sufficient force is applied to the slide portion so that it moves toward the base portion causing the one or more pins to project beyond the contact surface of the slide portion and engage one or more holes in the strap, thereby fixing the circumference of the belt at a preselected tension level.

16. The apparatus of claim 10, wherein the predetermined tension level is between approximately 100 N to 180 N.

17. The apparatus of claim 10, wherein the predetermined tension level is approximately 140 N.

18. A method of stabilizing a fractured pelvis comprising placing a belt around the greater trochanteric region of a person's fractured pelvis, the belt having a buckle device including one or more pin structures that remain concealed under a contact surface until sufficient force is exerted against the contact surface to make the one or more pins available for engaging one or more holes in a strap portion of the belt, pulling the strap portion against the contact surface until the one or more pins emerge from the contact surface and engage one or more holes in the strap portion, thereby automatically setting the belt at a tension level that has been predetermined to substantially stabilize a fractured pelvis without excessive compression.

19. The method of claim 18 further comprising tensioning the strap around the patient at a level between 100 N to 180 N.

20. The method of claim 18 further comprising tensioning the strap around the patient at a level of approximately 140 N.

21. The method of claim 18 wherein the strap portion is pulled in a first direction during the pulling step, the method further comprising pulling the buckle device in a second direction opposite from the first direction with approximately equivalent force to minimize significant shifting of the buckle device around the patient.

* * * * *